US00PP21302P2

(12) United States Plant Patent
Kraan

(10) Patent No.: US PP21,302 P2
(45) Date of Patent: Sep. 21, 2010

(54) ***HYDRANGEA* PLANT NAMED 'BOKRAPLUME'**

(50) Latin Name: *Hydrangea paniculata*
Varietal Denomination: Bokraplume

(75) Inventor: Kees Jan Kraan, Papenveer (NL)

(73) Assignee: Boot + Co. Boomkwekenijen B.V., Boskoop (NL)

( * ) Notice: Subject to any disclaimer, the term of this patent is extended or adjusted under 35 U.S.C. 154(b) by 63 days.

(21) Appl. No.: 12/315,154

(22) Filed: Nov. 28, 2008

(51) Int. Cl.
*A01H 5/00* (2006.01)

(52) U.S. Cl. ..... Plt./250

(58) Field of Classification Search ..... Plt./250
See application file for complete search history.

*Primary Examiner*—Wendy C. Haas
(74) *Attorney, Agent, or Firm*—C. A. Whealy

(57) ABSTRACT

A new and distinct cultivar of *Hydrangea* plant named 'Bokraplume', characterized by its compact and outwardly spreading plant habit; and inflorescences with white-colored flowers that with development become red purple in color.

3 Drawing Sheets

Botanical designation: *Hydrangea paniculata.*
Cultivar denomination: 'Bokraplume'.

BACKGROUND OF THE INVENTION

The present invention relates to a new and distinct cultivar of *Hydrangea plant*, botanically known as *Hydrangea paniculata* and hereinafter referred to by the name 'Bokraplume'.

The new *Hydrangea* plant is the product of an open-pollination occurring in July, 2003 in Boskoop, The Netherlands. The female, or seed, parent is an unnamed seedling selection of *Hydrangea paniculata*, not patented and the male, or pollen, parent is an unknown selection of *Hydrangea paniculata*. The new *Hydrangea* was discovered and selected by the Inventor as a single flowering plant within the progeny of the stated open-pollination in a controlled environment in Boskoop, The Netherlands during the summer of 2005.

Asexual reproduction of the new *Hydrangea* plant by vegetative cuttings in a controlled greenhouse environment in Boskoop, The Netherlands since the summer of 2005, has shown that the unique features of this new *Hydrangea* plant are stable and reproduced true to type in successive generations.

SUMMARY OF THE INVENTION

Plants of the new *Hydrangea* have not been observed under all possible environmental conditions. The phenotype may vary somewhat with variations in environment and cultural practices such as temperature and light intensity without, however, any variance in genotype. The following traits have been repeatedly observed and are determined to be the unique characteristics of 'Bokraplume'. These characteristics in combination distinguish 'Bokraplume' as a new and distinct cultivar of *Hydrangea:*

1. Compact and outwardly spreading plant habit.
2. Inflorescences with white-colored flowers that become red purple in color with development.

Plants of the new *Hydrangea* differ from plants of the female parent selection primarily in plant habit as plants of the new *Hydrangea* are more compact than plants of the female parent selection.

Plants of the new *Hydrangea* can be compared to plants of *Hydrangea* 'Bokratorch', disclosed in a U.S. Plant Pat. application Ser. No. 12/315,155. Plants of the new *Hydrangea* differ primarily from plants of 'Bokratorch' in the following characteristics:

1. Plants of the new *Hydrangea* are not as broad as plants of 'Bokratorch'.
2. Plants of the new *Hydrangea* have larger panicles than plants of 'Bokratorch'.
3. Plants of the new *Hydrangea* and 'Bokratorch' differ in sterile flower color.

Plants of the new *Hydrangea* can be compared to plants of *Hydrangea* 'Kyushu', not patented. Plants of the new *Hydrangea* differ primarily from plants of 'Kyushu' in the following characteristics:

1. Plants of the new *Hydrangea* are more compact than plants of 'Kyushu'.
2. Flowers of plants of the new *Hydrangea* become red purple in color with development whereas flowers of plants of 'Kyushu' become off-white to brown with development.

Plants of the new *Hydrangea* can also be compared to plants of *Hydrangea* 'Pink Diamond', not patented. Plants of the new *Hydrangea* differ primarily from plants of 'Pink Diamond' in the following characteristics:

1. Plants of the new *Hydrangea* are more compact than plants of 'Pink Diamond'.
2. Flowers of plants of the new *Hydrangea* become red purple in color with development whereas flowers of plants of 'Pink Diamond' become light red purple to purple pink with development.

BRIEF DESCRIPTION OF THE PHOTOGRAPHS

The accompanying colored photographs illustrate the unique appearance of the new cultivar, showing the colors as true as it is reasonably possible to obtain in colored reproductions of this type.

Colors in the photographs may differ from the color value cited in the detailed botanical description which accurately describe the colors of the new *Hydrangea.*

The photograph on the first sheet comprises a side perspective view of a typical plant of 'Bokraplume' grown in an outdoor nursery.

The photograph on the second sheet is a close-up view of a typical leaf of 'Bokraplume'.

The photograph at the top of the third sheet is a close-up view of a typical developing inflorescence of 'Bokraplume'.

The photograph at the bottom of the third sheet is a close-up view of a typical developed inflorescence of 'Bokraplume'.

DETAILED BOTANICAL DESCRIPTION

Plants used in the aforementioned photographs and in the following description were grown during the spring and summer in Boskoop, The Netherlands, in an outdoor nursery and under conditions which closely approximate commercial production conditions. During the production of the plants, day temperatures ranged from 14° C. to 30° C. and night temperatures ranged from 4° C. to 16° C. Plants of the new *Hydrangea* had been growing for four years when the photographs and description were taken. In the following description, color references are made to The Royal Horticultural Society Colour Chart, 2001 Edition, except where general terms of ordinary dictionary significance are used.

Botanical description: *Hydrangea paniculata* 'Bokraplume'.

Parentage:

*Female, or seed, parent.*—Unnamed seedling selection of *Hydrangea paniculata*, not patented.

*Male, or pollen, parent.*—Unknown selection of *Hydrangea paniculata*, not patented.

Propagation:

*Method.*—By softwood cuttings.

*Time to initiate roots.*—About 25 days at temperatures of 22° C.

*Time to produce a rooted young plant.*—About three months at temperatures of 18° C.

*Root description.*—Medium in thickness, moderately fleshy; light brown in color.

Plant description:

Form/growth habit.—Compact and outwardly spreading plant habit; broad inverted triangle. Moderately strong lateral branches; moderately vigorous growth habit.

*Plant height.*—About 73.3 cm.

*Plant diameter or area of spread.*—About 112.5 cm.

*Branching habit.*—Freely branching habit with about 23 lateral branches per plant; pinching enhances lateral branch development.

*Lateral branches.*—Length: About 55.4 cm. Diameter: About 6 mm Internode length: About 6.8 cm. Texture, developing: Sparsely pubescent. Texture, fully developed: Smooth, glabrous. Angle: About 45° from vertical. Strength: Strong. Color, developing: Between N186D and 187B. Color, fully developed: Close to 199A.

Foliage description:

*Arrangement.*—Opposite or in whorls of three, simple.

*Length.*—About 10.4 cm.

*Width.*—About 6.1 cm.

*Shape.*—Ovate to elliptic.

*Apex.*—Acute to short apiculate.

*Base.*—Obtuse.

*Margin.*—Senate.

*Texture, upper and lower surfaces.*—Pubescent; rugose.

*Venation pattern.*—Pinnate.

*Color.*—Developing leaves, upper surface: Close to 144A. Developing leaves, lower surface: Close to 144B. Fully expanded leaves, upper surface: Between 137A and 144A; venation, close to 147C. Fully expanded leaves, lower surface: Close to 138B; venation, between 147C and 48C.

*Petiole.*—Length: About 1.7 cm. Diameter: About 2 mm. Texture, upper and lower surfaces: Pubescent. Color, upper surface: Close to 152D; along margins, close to 187B. Color, lower surface: Close to 144C.

Flower description:

*Flower type and habit.*—Single fertile and sterile flowers arranged on terminal lacecap panicles; panicles roughly conical. Flowers face upright to outward.

*Fragrance.*—Sweet, moderate.

*Natural flowering season.*—Continuous flowering during the summer to the late summer in The Netherlands.

*Flower longevity.*—Fertile flowers last about one week on the plant and sterile flowers last about three weeks on the plant; fertile and sterile flowers persistent.

*Quantity of flowers.*—Freely flowering habit; about 450 fertile flowers and about 65 sterile flowers per panicle.

*Panicle height.*—About 13.9 cm.

*Panicle diameter.*—About 12.7 cm.

*Fertile flowers.*—Diameter: About 9 mm. Depth (height): About 8 mm. Flower buds: Length: About 4 mm. Diameter: About 3 mm. Shape: Broadly ovate. Color: Close to 155C flushed with close to 63D. Petals: Arrangement: About five in a single whorl. Length: About 4.5 mm Width: About 2 mm. Shape: Ovate. Apex: Acute. Base: Cuneate. Margin: Entire. Texture, upper and lower surfaces: Smooth, glabrous. Color: When opening, upper surface: Close to 155C. When opening, lower surface: Close to 155C slightly flushed with between 62D and 63D. Fully opened, upper surface: Close to N155A. Fully opened, lower surface: Close to 155A. Sepals: Not observed. Pedicels: Length: About 2 mm. Diameter: About 0.5 mm. Strength: Moderately strong. Texture: Smooth, glabrous. Color: Close to 155A. Reproductive organs: Stamens: Quantity per flower: About eight. Filament length: About 4 mm. Filament color: Close to N155A. Anther shape: Reniform. Anther length: About 1 mm. Anther color: Close to 155A to 155B. Pollen amount: Scarce. Pollen color: Close to 158C to 158D. Pistils: Pistil quantity per flower: About three. Pistil length: About 2.5 mm. Stigma shape: Flattened. Stigma color: Close to 155A. Style length: About 2 mm. Style color: Close to 155C. Ovary color: Close to 155A.

*Sterile flowers.*—Diameter: About 3.4 cm. Depth (height): About 6 mm. Flower buds: Length: About 7 mm. Diameter: About 4 mm. Shape: Broadly ovate. Color: Close to 150D becoming closer to 157A with development. Petals: Arrangement: About four in a single whorl. Length: About 3.5 mm. Width: About 1.5 mm. Shape: Ovate. Apex: Acute. Base: Cuneate. Margin: Entire. Texture, upper and lower surfaces: Smooth, glabrous. Color: When opening, upper surface: Close to 155C. When opening, lower surface: Close to 155C slightly flushed with close to 62C to 62D. Fully opened, lower surface: Close to 155C flushed with close to 62C to 62D. Sepals: Arrangement: About four or five in a single whorl. Length:

About 1.7 cm. Width: About 1.5 cm. Shape: Broadly obovate. Apex: Recuse to rounded. Base: Cuneate. Margin: Entire. Texture, upper and lower surfaces: Smooth, glabrous. Color: When opening, upper surface: Close to 157C to 157D. When opening, lower surface: Close to 157D. Fully opened, upper surface: Close to 157D; towards the apex, close to 62D; color becoming closer to 185B with development. Fully opened, lower surface: Close to 157D; color becoming closer to between 150D to 160D flushed with close to 185D. Pedicels: Length: About 2 cm. Diameter: About 1 mm. Strength: Moderately strong. Texture: Smooth, glabrous. Color: Close to 155A to 155B. Reproductive organs: Stamens: Quantity per flower: About eight. Filament length: About 3 mm. Filament color: Close to N155A. Anther shape: Reniform. Anther length: About 1 mm. Anther color: Close to 155A. Pollen amount: Scarce. Pollen color: Close to 158C to 158D. Pistils: Not observed.

*Fruits/seeds.*—Fruit and seed development have not been observed on plants of the new *Hydrangea.*

Disease/pest resistance: Plants of the new *Hydrangea* have not been observed to be resistant to pathogens or pests common to *Hydrangea.*

Temperature tolerance: Plants of the new *Hydrangea* have been shown to be tolerant to temperatures ranging from about −20° C. to about 35° C.

It is claimed:

1. A new and distinct *Hydrangea* plant named 'Bokraplume' as illustrated and described.

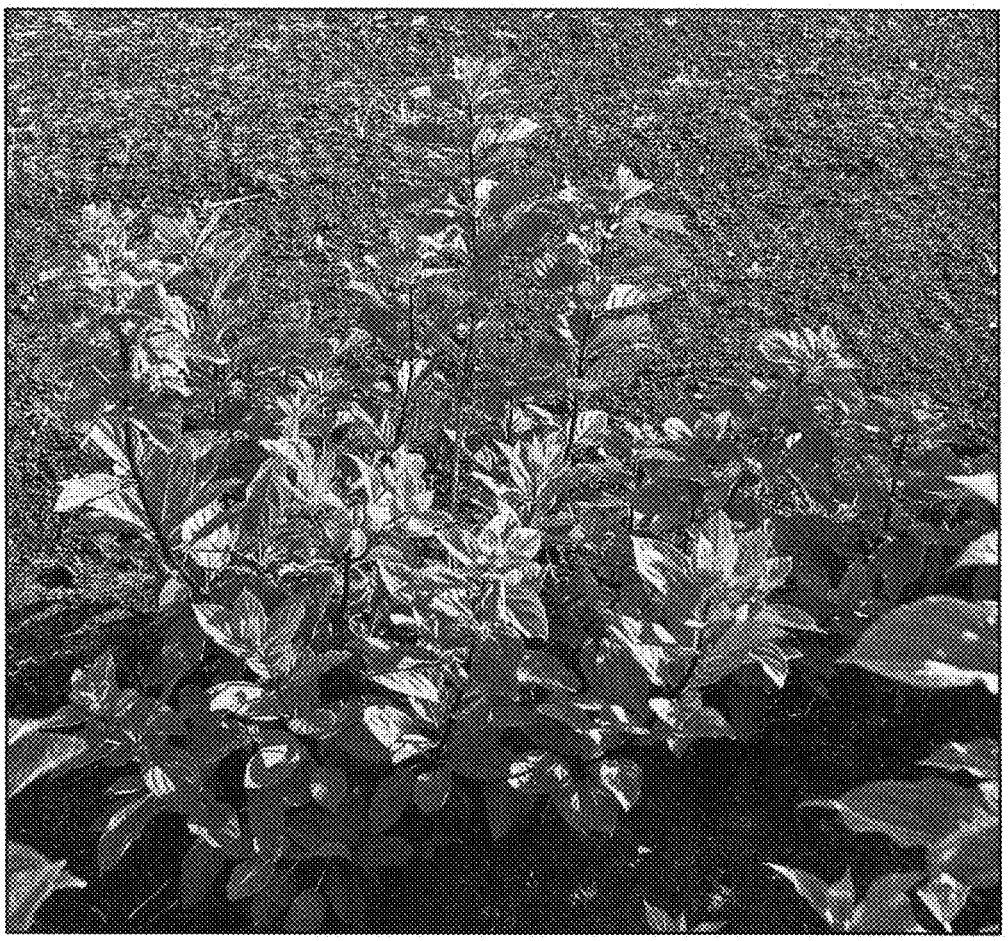

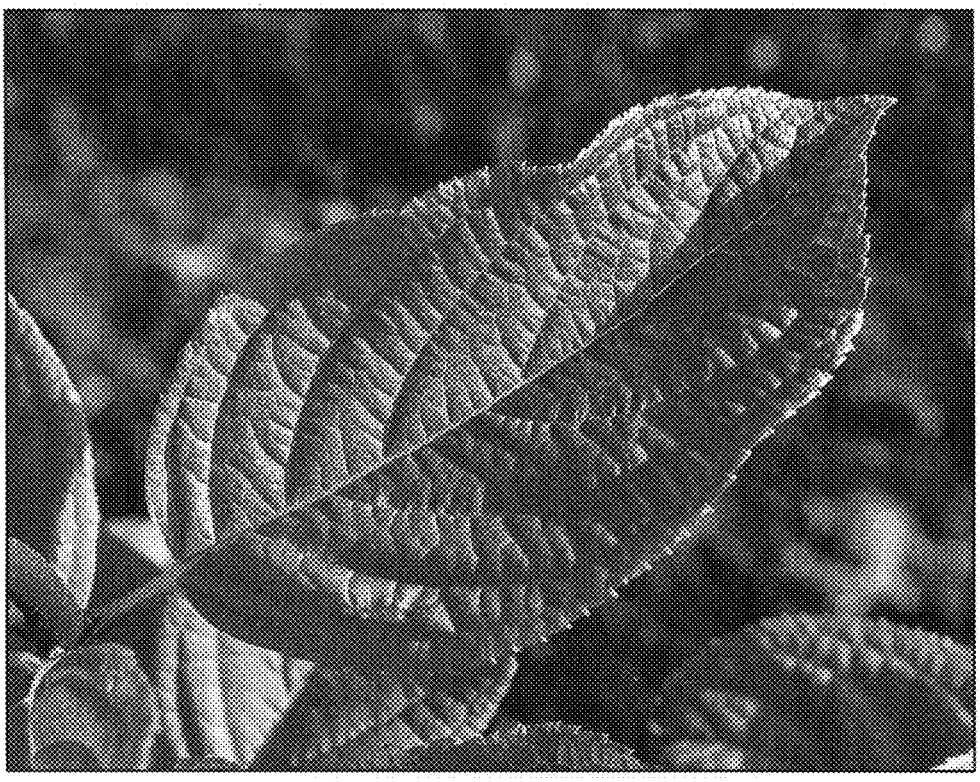

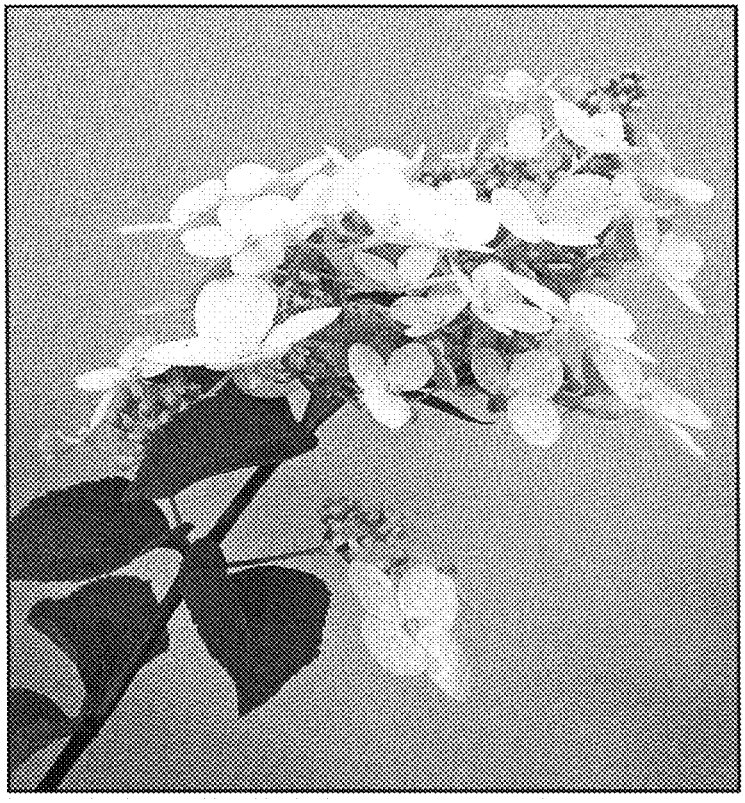
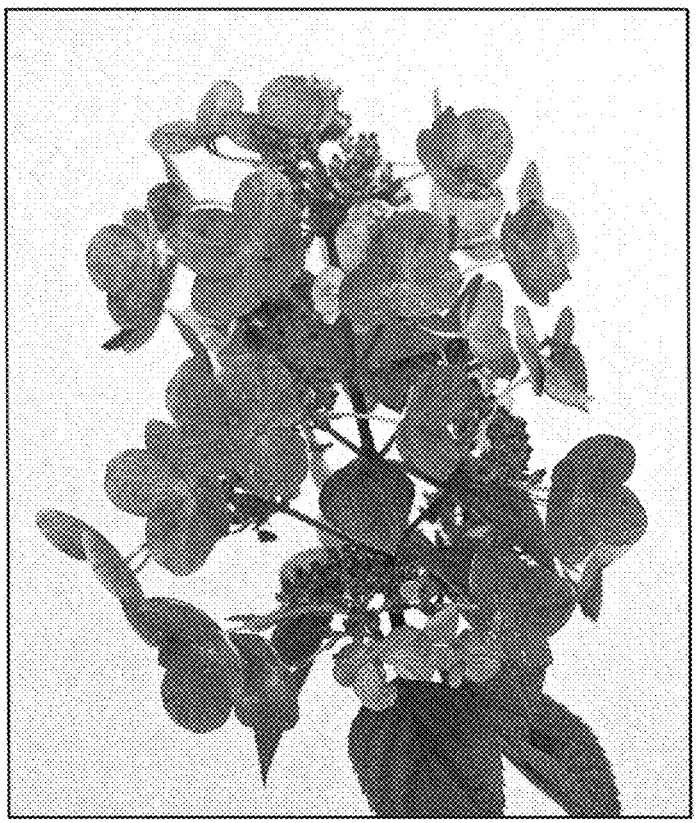

* * * * *